United States Patent [19]

Leimgruber et al.

[11] 3,965,141

[45] June 22, 1976

[54] PROCESS FOR PRODUCING DIALKYL AMINOACRYLONITRILE

[75] Inventors: Willy Leimgruber, Montclair; Manfred Weigele, North Caldwell, both of N.J.

[73] Assignee: Hoffmann-La Roche Inc., Nutley, N.J.

[22] Filed: May 2, 1975

[21] Appl. No.: 574,163

Related U.S. Application Data

[62] Division of Ser. No. 480,660, June 19, 1974, Pat. No. 3,900,511, which is a division of Ser. No. 338,018, March 5, 1973, Pat. No. 3,853,946, which is a division of Ser. No. 197,968, Nov. 11, 1971, Pat. No. 3,742,015, which is a division of Ser. No. 42,528, June 1, 1970, Pat. No. 3,655,716, which is a division of Ser. No. 719,834, April 9, 1968, Pat. No. 3,542,848.

[52] U.S. Cl............................................ 260/465.5 R

[51] Int. Cl.$^2$........................................ C07C 120/00
[58] Field of Search................................ 260/465.5 R

[56] References Cited

OTHER PUBLICATIONS

Sittig, "Acrylonitrile," *Chemical Process Monograph*, No. 14, 1965, pp. 58–60.

*Primary Examiner*—Joseph P. Brust
*Attorney, Agent, or Firm*—Samuel L. Welt; Bernard S. Leon; William H. Epstein

[57] ABSTRACT

A process for producing a dialkyl aminoacrylonitrile by treating dimethylaminopropionitrile with a hydrogen acceptor in the presence of a dehydrogenation catalyst. The dialkylaminoacrylonitrile thus produced is converted to aminomethylene malonitrile, a known intermediate for thiamine.

1 Claim, No Drawings

PROCESS FOR PRODUCING DIALKYL AMINOACRYLONITRILE

CROSS REFERENCE TO RELATED APPLICATIONS

This application is a divisional application of Ser. No. 480,660, filed June 19, 1974, now U.S. Pat. No. 3,900,511, issued Aug. 19, 1975, which in turn is a divisional application of Ser. No. 338,018 filed March 5, 1973, now U.S. Pat. No. 3,853,946 issued Dec. 10, 1074 which in turn is a divisional application of Ser No. 197,968, filed Nov. 11, 1971, now U.S. Pat. No. 3,742,015 issued June 26, 1973, which in turn is a divisional application of our U.S. Pat. application Ser. No. 42,528, filed June 1, 1970, now U.S. Pat. No. 3,655,716, issued Apr. 11, 1972, which in turn is a divisional application of our U.S. patent application Ser. No. 719,834, filed Apr. 9, 1968, now U.S. Pat. No. 3,542,848, issued Nov. 24, 1970.

BACKGROUND OF THE INVENTION

The synthesis of thiamine has been described by a number of investigators such as Todd and Bergell in *Journ. Chem. Soc.*, pg. 364 (1937). In these syntheses a pyrimidine ring compound, i.e., 2-methyl-2-amino-5-bromomethylpyrimidine dihydro-bromide and a thiazole ring compound, i.e., 4-methyl-5-β-hydroxyethyl thiazide are condensed to form the thiamine ring structure. This pyrimidine compound is prepared from 2-methyl-4-amino-5-cyanopyrimidine which is formed by the condensation of aminomethylene malononitrile with acetimino ethyl ether, as described in Chapter 16 of the *Vitamins, Chemistry, Physiology, Pathology*, Vol. III, Sebrell and Harris, Academic Press, Inc., New York (1954).

This procedure therefore depends on the use of the aminomethylene malononitrile which has been a difficult material to synthesize economically. In view of this fact, it has long been desired to provide an economical means of synthesizing aminomethylene malononitrile utilizing inexpensive and readily available starting materials.

SUMMARY OF THE INVENTION

In accordance with this invention, it has been found that aminomethylene malononitrile, which has the formula:

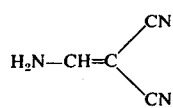

can be synthesized economically from a dialkyl aminoacrylonitrile of the formula:

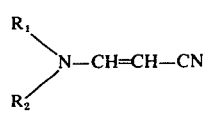

wherein $R_1$ and $R_2$ are lower alkyl.

In accordance with another embodiment of this invention, we have found that the starting material of formula II can be easily synthesized from readily available and commercially economical materials by two methods. In the first method of producing the compound of formula II above, an acetal compound of the formula:

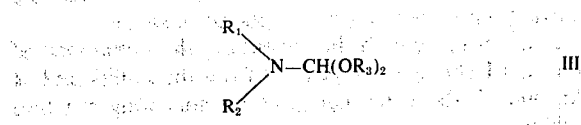

wherein $R_1$ and $R_2$ are as above, and $R_3$ is lower alkyl, is condensed at a temperature of at least 80°C. with acetonitrile. In accordance with the second method of producing the compound of formula II above, a compound of the formula:

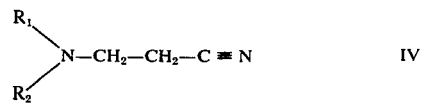

wherein $R_1$ and $R_2$ are as above, is treated with a hydrogen acceptor at a temperature of at least 50°C. in the presence of a dehydrogenation catalyst.

DETAILED DESCRIPTION

As used throughout the specification, the term "lower alkyl" includes both straight and branched chain alkyl groups containing from 1 to 6 carbon atoms such as methyl, ethyl, propyl, isopropyl, and the like. As used throughout the specification, the term "lower alkanoyl" includes alkanoyl groups containing from 2 to 6 carbon atoms such as acetyl, propionyl, and butyryl.

The reaction of acetonitrile with the acetal of formula III to form the compound of formula II is carried out at a temperature of at least 80°C. Generally, it is preferred to utilize a temperature of from 100°C. to 250°C. in carrying out this reaction. While this reaction can be carried out at atmospheric pressure, superatmospheric pressures are utilized when higher temperatures are utilized. This reaction can be carried out without the need for utilizing any solvent. However if desired, an inert organic solvent can be utilized. Any conventional inert organic solvent such as benzene, toluene, methylene chloride, can, if desired be utilized in carrying out this reaction.

The second method of preparing the compound of formula II above is by treating a compound of formula IV above with a hydrogen acceptor at a temperature of at least 50°C. in the presence of a dehydrogenation catalyst. Any conventional dehydrogenation catalyst can be utilized in carrying out this reaction. Among the preferred dehydrogenation catalysts which can be utilized in this reaction are palladium, Raney nickel and cupric chromite. In carrying out this reaction, any conventional hydrogen acceptor can be utilized. Among the preferred hydrogen acceptors is oxygen which can be supplied by carrying out the reaction in the presence of air. Alternatively, the oxygen can be supplied in the form of bottled oxygen. Other hydrogen acceptors which can be advantageously utilized in this process are aliphatic ethers containing at least one ethylenic moiety bound to the oxygen atom and having from 3 to 15 carbon atoms such as methyl vinyl ether and cyclic ethers such as dihydropyran.

In converting the compound of formula IV above to the compound of formula II above, no solvent need be present. Generally, in carrying out this reaction, a temperature of at least 50°C. should be utilized with temperatures of between 80°C. to 200°C., being preferred. If high temperatures are utilized, the reaction may be carried out under superatmospheric pressure.

In accordance with this invention, the compound of formula I above is synthesized from the compound of formula II above by means of the following reaction scheme:

out, as in reaction step (a), by treating the compound of the formula II above with a diloweralkyl formamide in the presence of an inorganic acid halide condensing agent. These three reactants may be used in any molar ratio in carrying out the reaction of step (a). In carrying out the reaction of step (a), temperatures of from about −10°C. to +10°C. should be utilized. Generally, it is preferred to carry out the reaction of step (a) in the presence of an inert organic solvent. Any conventional

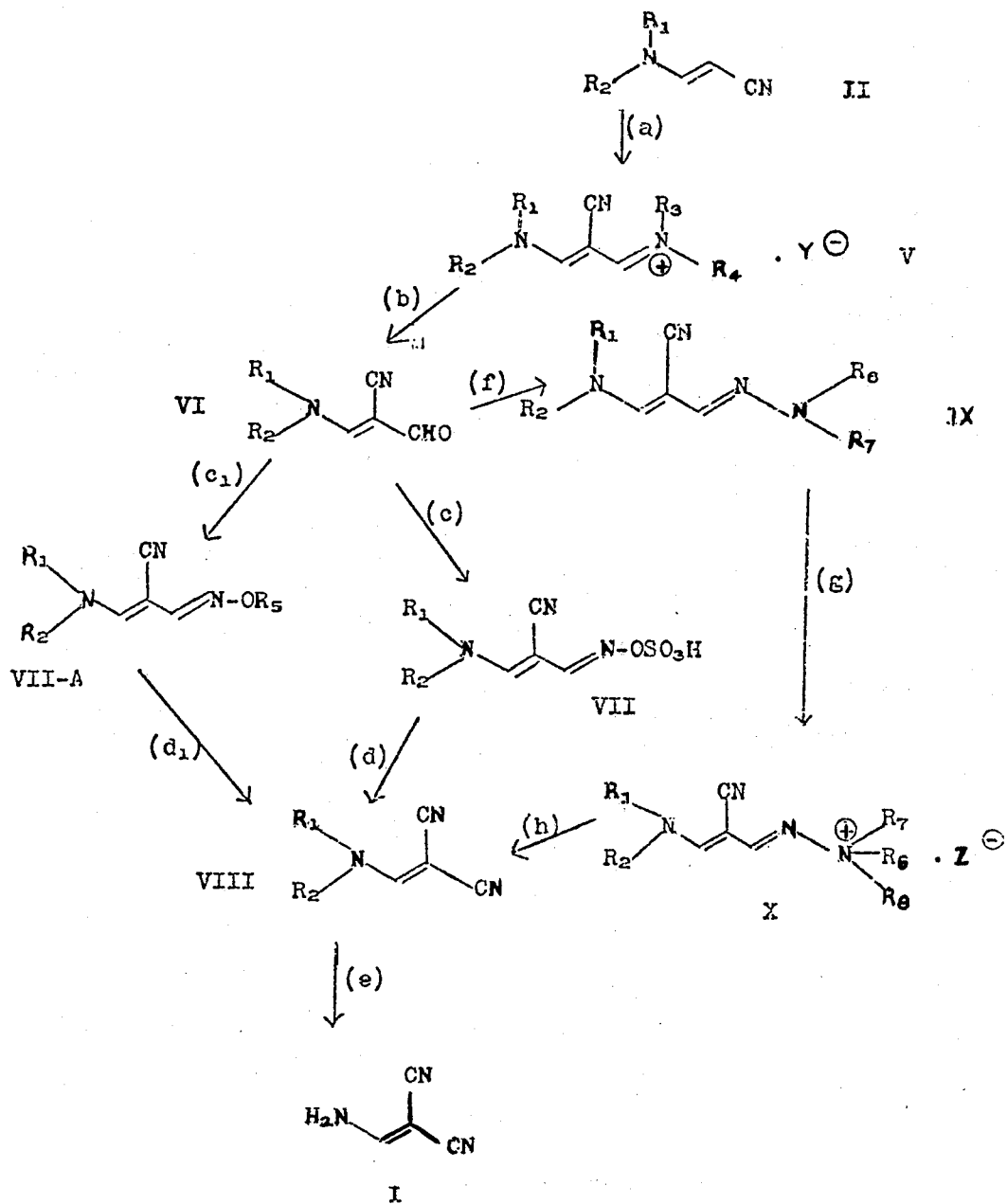

wherein $R_1$ and $R_2$ are as above, $R_3$, $R_4$, $R_6$, $R_7$ and $R_8$ are lower alkyl, $Y^-$ is a halide ion, and $R_5$ is lower alkanoyl, and $Z^-$ is the $CH_3OSO_3$ ion.

The conversion of compounds of the formula II above to compounds of the formula V above is carried inert organic solvent can be utilized However, the preferred solvents are the halogenated hydrocarbons such as chloroform, dichloromethane, 1,2-dichloroethane, etc. In carrying out this reacton, any of the lower alkyl formamides, preferably dimethyl formamide can be utilized. Among the preferred inorganic acid halide condensing agents which can be utilized in accordance with this invention are included phophorous oxychloride, phosgene, thionyl chloride, phosphorous pentachloride, etc.

The compound of formula V above is converted into the compound of formula VI above, as in reaction step (b), by raising the pH of an aqueous solution containing the compound of formula V above to a value of from 7 to 9. This is accomplished by treating the compound of formula V above with an aqueous alkaline medium sufficient to raise the pH to a range of from 7 to 9. Any conventional inorganic base such as sodium hydroxide, potassium hydroxide, etc. can be utilized as the alkaline medium to provide a pH within the range of from about 7 to 9. In carrying out this reaction, temperature and pressure are not critical and this reaction can be carried out at room temperature and atmospheric pressure. If desired, elevated or reduced temperatures can be utilized.

The compound of formula VI above is converted to the compound of formula VII-A above, via reaction step ($c_1$), by means of reacting the compound of the formula VI above with a compound of the formula:

  NH$_2$OR$_5$    XI wherein R$_5$ is as above.

In the reaction of step ($c_1$), the two reactants may be used in any molar ratio. The reaction of step ($c_1$) is carried out in the presence of an inert organic solvent. Any conventional inert organic solvent can be utilized. Among the inert organic solvents that can be utilized are included halogenated hydrocarbons such as chloroform, dichloromethane, 1,2-dichloroethane, etc. Generally, in carrying out this reaction, room temperature is utilized. During the reaction of step ($c_1$), the temperature utilized should not be above 30°C. It is preferred to carry out this reaction at a temperature of from about 0°C. to 25°C.

The compound of formula VII-A can be converted to the compound of formula VIII via reaction step ($d_1$) by heating the compound of formula VII-A to a temperature of from 70°C. to 90°C. The reaction of step ($d_1$) is carried out in the presence of an inert organic solvent. Any of the solvents hereinabove mentioned in connection with reaction step ($c_1$) can be utilized in carrying out the reaction of step ($d_1$).

The compound of formula VI above can be converted to the compound of formula VII, via reaction step (c) by means of reacting the compound of the formula VI with a compound of the formula:

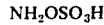  NH$_2$OSO$_3$H    XI-A

This reaction is preferably carried out by suspending the two reactants in water and allowing the reaction to proceed at room temperature. During the reaction of step (c), the temperature utilized should not exceed about 30°C. Generally, it is preferred to utilize a temperature of from 0°C. to 25°C. in this reaction.

The compound of formula VII above can be converted to the compound of formula VIII, as in reaction step (d) by adjusting the pH of the aqueous reaction mixture containing the compound of formula VII to about 5.5 to 8.5 and warming the reaction mixture to a temperature of from about 60°C. to 90°C. The pH of the reaction mixture is adjusted to a range of 5.5 to 8.5 by treating the aqueous mixture with an alkali such as an alkali metal hydroxide. Among the preferred alkali are included sodium hydroxide, potassium hydroxide, etc.

The conversion of compounds of the formula VI above to the compound of the formula IX above is carried out, as in reaction step (f), by treating the compound of the formula VI above with a hydrazine of the formula:

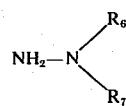

XII wherein R$_6$ and R$_7$ are as above. In carrying out the reaction step (f) any mole ratio of the reactants can be utilized. Generally, this reaction is carried out in the presence of an inert organic solvent. Any conventional inert organic solvent can be utilized. Among the preferred solvents are included the lower alkanols, such as methanol, ethanol, etc. In carrying out this reaction, temperature and pressure are not critical and this reaction can be carried out at room temperature and atmospheric pressure. However, it is preferred to carry out this reaction at the reflux temperature of the solvent. Therefore, temperatures of from 50°C. to 100°C. are generally utilized, depending upon the reflux temperature of the solvent.

The conversion of compounds of the formula IX above to the compounds of the formula X above, via reaction step (g), is carried out by treating the compound of the formula IX above with a dilower alkyl sulfate. Generally, this reaction is carried out in the presence of an inert organic solvent. Any conventional inert organic solvent can be utilized in carrying out this reaction. Among the conventional inert organic solvents which can be utilized are included lower alkanols, such as methanol or ethanol. In carrying out this reaction, temperature and pressure are not critical and this reaction can be carried out at room temperature and atmospheric pressure or at elevated temperatures. Generally, it is preferred to carry out this reaction at the reflux temperature of the solvent.

The compound of formula X is converted to the compound of formula VIII via reaction step (h) by treating the compound of formula X above with an alkali. Any conventional alkali such as an alkali metal hydroxide or an alkali metal lower alkoxide, can be utilized in carrying out this reaction. Among the preferred alkali are included sodium hydroxide, potassium hydroxide, sodium methoxide, etc. This reaction is carried out in the presence of an inert organic solvent. Among the solvents that can be utilized are the lower alkanols, such as methanol or ethanol. In carrying out this reaction, temperature and pressure are not critical and this reaction can be carried out at room temperature and at atmospheric pressure. If desired, elevated temperatures such as 80°C. can be utilized in carrying out this reaction.

The compound of formula VIII above is converted into the compound of formula I above by treating the compound of formula VIII above, as in reaction step (e), with liquid ammonia. This reaction is generally carried out a temperature of from minus 70°C. or below. It is preferred to carry out this reaction at a temperature of from minus 70°C. to minus 120°C. This reaction is carried out by dissolving the compound of formula VIII above in liquid ammonia. After the compound of formula VIII is dissolved in liquid ammonia, the resulting solution is slowly warmed to room temperature so as to produce the compound of formula I above. This warming should take place within a period of time of at least one hour. Generally, it is preferred to carry out this warming step within a period of from 4 to 24 hours.

Another means of converting the compound of formula VIII above into the compound of the formula I above is by treating the compound of the formula VIII above with a saturated aqueous solution of ammonium hydroxide. This reaction is carried out in an aqueous medium and by heating the aqueous mixture containing the compound of formula VIII and ammonium hydroxide to a temperature of from about 80°C. to 100°C.

This invention will be more fully understood from the specific examples which follow. These examples are intended to illustrate the invention and are not to be construed as limitative thereof. All temperatures are in degrees centigrade.

EXAMPLE 1

Dehydrogenation of dimethylaminopropionitrile to dimethylaminoacrylonitrile

The catalytic dehydrogenation of dimethylaminopropionitrile was carried out under the following conditions:

| Hydrogen Acceptor | Catalyst | Reaction Temperature | | Reaction Time |
|---|---|---|---|---|
| Air | 10% Raney nickel | Reflux: 115°C. | about | 6 hours |
| Air | 30% GuCr$_2$O$_4$ | | | 3-24 hours |
| CH$_2$=CHOCH$_2$CH$_3$ | palladium on carbon (10%) | 50°C. | | 24 hours |
| Dihydropyran | palladium on carbon (10%) | Reflux: 80°C. | about | 24 hours |
| Dihydropyran | palladium on carbon (10%) | Reflux | | 40 hours |

In the above reaction, a reaction mixture was prepared containing the catalyst and dimethylaminopropionitrile. Where an ether hydrogen acceptor was utilized, the hydrogen acceptor was present in a molar amount of ten times the moles of dimethylaminopropionitrile in the reaction mixture and the reaction was carried out under nitrogen. In the cases where air was used, the reaction was carried out by exposing the reaction mixture to the atmosphere. The catalyst was present in an amount of about 10% by weight or 30% by weight based upon the weight of the dimethylaminopropionitrile as indicated above. The final product obtained by vapor phase chromatography was dimethylaminoacrylonitrile. This product distilled at 115°C. at 3mm Hg.

EXAMPLE 2

Preparation of 3-dimethylaminoacrylonitrile 173.0 g. Of the diethylacetal of dimethylformamide (1.18 moles) and 400 ml. of acetonitrile were placed in a 1200 ml. autoclave. Air was removed from the autoclave by flushing with nitrogen, and after purging charged to 50 p.s.i. with nitrogen. The reaction was carried out for 36 hours at 150°C. Upon completion of the reaction, excess acetonitrile was removed by vacuum distillation using a rotary evaporator at a vacuum of 135 mm Hg. and a waterbath temperature of 60°C. maximum. The remaining residue was fractionated using a 24 inch Vigreaux column. After discarding a small first fraction, the material boiling at 115°C. and 3.0 mm Hg was collected. This material was 3-dimethylaminoacrylonitrile.

EXAMPLE 3

Preparation of (3-dimethylamino-2-cyano-2-propen-1-ylidene)-dimethylammonium perchlorate 10 ml. Of N,N-dimethylformamide were stirred at −4° to −7° and 10 ml. of phosphoroxy chloride were added dropwise in such a rate as to maintain the reaction temperature below 0°. The resulting semi-solid reaction mixture was diluted with 80 ml. of 1,2-dichloroethane. On warming to room temperature, a clear amber solution was obtained. The solution was cooled to −8° to −10°C. and 5.91 g. of 3-dimethylamino-acrylonitrile, dissolved in 15 ml. of 1,2-dichloroethane were added dropwise with stirring within 15 minutes. After removal of the solvent in vacuo a semicrystalline residue was obtained. The material was dissolved in 20 g. of ice/water and 8.1 g. of sodium perchlorate were added to this solution. On cooling (3-dimethylamino-2-cyano-2-propen-1-ylidene)-dimethylammonium perchlorate as crystals, (m.p. 139°–142°) was obtained.

EXAMPLE 4

Preparation of 2-cyano-3-dimethylaminoacrolein 36 ml. (0.465 mole) Of N,N-dimethylformamide were stirred at 0° and 36 ml. (0.392 mole) of phosphorus oxychloride were added dropwise (a salt/ice bath was used in order to keep the reaction mixture at 0°). To the stirring semi-solid, faintly colored reaction mixture was added 300 ml. of 1,2-dichloroethane. Upon warming to room temperature by means of a water bath (25°), a clear solution resulted which was cooled to −7° with an ice/salt bath. A solution of 30 ml. (0.293 mole) of β-dimethylaminoacrylonitrile in 90 ml. of 1,2-dichloroethane was added dropwise keeping the temperature between −4° to −7°. The addition required about 1 hour. The cooling bath was removed and the clear amber reaction mixture allowed to come to room temperature. The reaction mixture was transferred to a 2 liter, round bottomed flask and the solvent removed in vacuo leaving a semi-solid orange colored residue. A 100 g. of ice was added to the residue which gradually dissolved with evolution of heat. The solution was transferred to a beaker and the pH adjusted to 8.4 by adding carefully 2N sodium hydroxide (815 ml. were required) to the stirred solution at 15°–20°. The resulting solution was extracted with ethyl acetate in a liquid-liquid extractor overnight. The ethyl acetate extract was cooled, the crystals which had separated were filtered off, washed with cold ethyl acetate and dried in vacuo, affording crude 2-cyano-3-dimethylaminoacrolein, as deep yellow prisms, m.p. 143°–144°. This material was dissolved in 500 ml. of hot water, treated with 2 g. of norite, the solvent removed in vacuo and the residue crystallized from absolute ethanol; producing the pure product in the form of light yellow prisms, m.p. 143°–144°.

EXAMPLE 5

Preparation of 2-cyano-3-dimethylaminoacrolein

Into a 250 ml. 3-neck-round-bottom flask were placed 7.3 g. (0.1m) of dimethylformamide and 150 ml. dichloromethane. The stirred solution was cooled in ice/water and phosgene was bubbled through for 30 minutes. A white solid formed. The solvent was removed in vacuo. The remaining solid was suspended in 120 ml. dichloromethane. Th stirred suspension was cooled in an ice/salt bath to −10°C. A solution of 9.6 g. (0.1m) 3-dimethylaminoacrylonitrile in 40 ml. of dichloromethane was added dropwise, maintaining the temperature below 0°C. After completed addition a clear yellow solution resulted. The solution was evaporated in vacuo to dryness. The solid residue was dissolved in 20 ml. of water. The aqueous solution was cooled to 0°C. and adjusted to pH 8.5 with 5N sodium hydroxide solution. The alkaline solution was allowed to stand at room temperature for 4 hours, during which time a crystalline solid precipitated. The whole mixture was extracted with 5 × 100 ml. of dichloromethane. The combined organic extracts were dried over magnesium sulfate and evaporated to dryness in vacuo. The crystalline residue consisted of 2-cyano-3-dimethylaminoacrolein, m.p. 140°–141°. After recrystallization from ethanol, the melting point was 142°–143.5°.

EXAMPLE 6

Preparation of dimethylaminomethylenemalononitrile

To a mixture of 10 g. of 2-cyano-3-dimethylaminoacrolein and 100 ml. of ethylene chloride was added in small portions with stirring 9 g. of 0-acetylhydroxylamine hydrochloride. The mixture was stirred at room temperature for 30 minutes and then heated at reflux temperature for 1 hour. On cooling, dimethylaminomethylenemalononitrile crystallized from the reaction solution, and was collected by filtration (m.p. 81°–82°).

EXAMPLE 7

Preparation of N-(3-dimethylamino-2-cyano-2-propene-1-ylidene)-N',N'-dimethylhydrazine hydrochloride A solution of 12.4 g. of 2-cyano-3-dimethylaminoacrolein and 9.6 g. of 1,1-dimethylhydrazine hydrochloride in 50 ml. of methanol was heated to reflux temperature for 90 minutes. On cooling the reaction mixture a first crop of N-(3-dimethylamino-2-cyano-2-propene-1-ylidene)-N',N'-dimethylhydrazine hydrochloride (m.p. 173°) precipitated in crystalline form and was filtered off. A second crop (m.p. 170°–172°) was obtained from the mother liquor on concentrating.

EXAMPLE 8

Preparation of N-(3-dimethylamino-2-cyano-2-propene-1-ylidene)-N',N'-dimethylhydrazine 5g. Of the N-(3-dimethylamino-2-cyano-2-propene-1-ylidene)-N',N'-dimethylhydrazine hydrochloride was dissolved in the minimum required amount of water. The pH was adjusted to 8 by addition of 10% sodium hydroxide solution. The desired product N-(3-dimethylamino-2-cyano-2-propene-1-ylidene)-N',N'-dimethylhydrazine precipitated and was filtered off (m.p. 130°–134°).

EXAMPLE 9

Preparation of N-(3-dimethylamino-2-cyano-2-propen-1-ylidene)-N',N',N'-trimethylhydrazinium methyl sulfate 3.3 g. Of N-(3-dimethylamino-212-cyano-2-propen-1-ylidene)-N',N'-dimethylhydrazine were dissolved in 20 ml. of absolute ethanol. The solution was heated on a steambath, and 1.9 ml. of dimethyl sulfate was added. The resulting mixture was allowed to cool to room temperature and was then refrigerated. The product N-(3-dimethylamino-2-cyano-2-propen-1-ylidene)N',-N',N'-trimethylhydrazinium methyl sulfate was collected by filtration (m.p. 147°–149°).

EXAMPLE 10

Preparation of dimethylaminomethylenemalononitrile

To a solution of 2.92 g. of N-(330-dimethylamino-2-cyano-2-propen-1-ylidene)N',N',N'-trimethylhydrazinium methyl sulfate in 20 ml. of methanol was added in small portions at room temperature 540 mg. of sodium methoxide. The resulting mixture was stirred at room temperature for 30 minutes, then the solvent was evaporated under reduced pressure. The residue was dissolved in hot water. On cooling dimethylaminomethylenemalononitrile crystallized out and was collected by filtration (m.p. 81°–83°).

EXAMPLE 11

Preparation of dimethylaminomethylenemalononitrile

To a slurry of 12.4 g. of 2-cyano-3-dimethylaminoacrolein in 50 ml. of water was added in small portions 13.6 g. of hydroxylamine-0-sulfonic acid (91% pure). The resulting clear solution was stirred for an additional 10 minutes, then cooled to 0° and adjusted to pH 6.0 by addition of approximately 26 ml. of 5N sodium hydroxide solution. The mixture was heated for 20 minutes in a water bath at 70°. A pH 3 was maintained over this period by dropwise addition of 5N sodium hydroxide solution. After cooling to room temperature, the mixture was extracted with 3 × 100 ml. of methylene chloride. The combined extracts were washed with 50 ml. of water, dried over magnesium sulfate, filtered and evaporated to dryness under reduced pressure. Thus, dimethylaminomethylenemalononitrile was obtained. After recrystallization from isopropanol, the material had a melting point of 93°–95°.

EXAMPLE 12

Preparation of dimethylaminomethylenemalononitrile from 3-dimethylaminoacrylonitrile Into a 250 ml. 3-neck-round-bottom flask are placed 7.3 g. (0.1m) of dimethylformamide and 150 ml. of dichloromethane. The stirred solution is cooled in ice/water and phosgene is bubbled through for 30 minutes. A white solid forms. The solvent is removed under reduced pressure. The remaining solid is suspended in 120 ml. of dichloromethane. The stirred suspension is cooled in an ice/salt bath to −10°. A solution of 9.6 g. (0.1m) of 3-dimethylaminoacrylonitrile in 40 ml. of dichloromethane is added dropwise, maintaining the temperature below 0°. After completed addition a clear yellow solution results. The solution is evaporated to dryness under reduced pressure. The remaining yellow solid is dissolved in 20 ml. of water. The aqueous solution is cooled to 0° and adjusted to pH 8 with 5N sodium hydroxide (∼15 ml.). The alkaline solution is allowed to stand at room temperature for 90 minutes. A crystalline solid precipitates. The slurry is diluted with 20 ml. of water, and, while stirring 12.5 g. (0.1m) of hydroxylamino-0-sulfonic acid (91–93% pure) is added as a solid. A clear solution results. After 10 minutes stirring at room temperature, the solution is cooled in ice/water and the pH is adjusted to 7 with 5N sodium hydroxide (∼26 ml.). The neutral solution is heated briefly to 75° (∼3–4 min.). On cooling the main fraction of dimethylaminomethylenemalononitrile precipitates in crystalline form. The aqueous mother liquor is readjusted to pH 7 and extracted with 3 × 100 ml. of dichloromethane. The combined organic extracts are dried over magnesium sulfate and evaporated to dryness. The residue is dissolved in 50 ml. of isopropanol. The resulting solution is treated with activated charcoal and filtered hot. On concentration of the solution an additional crop of dimethylaminomethylenemalononitrile is obtained.

EXAMPLE 14

Preparation of Aminomethylenemalononitrile

Into a flask, cooled in a dry ice/actone bath was placed 200 mg. of dimethylaminomethylenemalononitrile. 30 ml. of ammonia was condensed into the flask. The resulting solution was allowed to come slowly to room temperature and to evaporate over a period of ca. 10 hours. The dry residue was recrystallized from water. Thus, aminomethylenemalononitrile (m.p. 139°–144°) was obtained.

We claim:

1. A process for producing a dialkylaminoacrylonitrile having the formula:

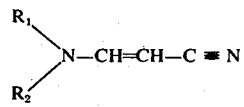

wherein $R_1$ and $R_2$ are lower alkyl containing from 1 to 6 carbon atoms;
comprising treating a compound of formula:

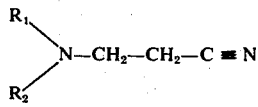

wherein $R_1$ and $R_2$ are as above; with a hydrogen acceptor at a temperature of from 50°C. to 200°C. in the presence of a dehydrogenation catalyst.

* * * * *